United States Patent
Reichelt et al.

(10) Patent No.: US 7,108,727 B2
(45) Date of Patent: Sep. 19, 2006

(54) REACTIVE DYES AND THE USE THEREOF FOR DYEING SUBSTRATES CONTAINING NUCLEOPHILIC GROUPS

(75) Inventors: Helmut Reichelt, Neustadt (DE); Günther Seybold, Neuhofen (DE); Manfred Patsch, Wachenheim (DE); Gunter-Rudolf Schröder, Mannheim (DE); Stevan David Jones, Guildford (GB); James Charles Dunbar, Morrow, OH (US); Colin John Clarke, Whitton (GB)

(73) Assignee: BASF Aktiengellschaft, Ludwigshafen (DE)

( * ) Notice: Subject to any disclaimer, the term of this patent is extended or adjusted under 35 U.S.C. 154(b) by 83 days.

(21) Appl. No.: 10/469,600

(22) PCT Filed: Mar. 5, 2002

(86) PCT No.: PCT/EP02/02385

§ 371 (c)(1),
(2), (4) Date: Sep. 3, 2003

(87) PCT Pub. No.: WO02/070610

PCT Pub. Date: Sep. 12, 2002

(65) Prior Publication Data

US 2004/0088804 A1    May 13, 2004

(30) Foreign Application Priority Data

Mar. 5, 2001  (DE) ............................... 101 10 552

(51) Int. Cl.
*D06P 1/38* (2006.01)
*A61K 7/13* (2006.01)

(52) U.S. Cl. .................................. 8/428; 8/543; 8/549

(58) Field of Classification Search .................. 8/404, 8/405, 414, 410, 411, 428, 543
See application file for complete search history.

(56) References Cited

U.S. PATENT DOCUMENTS

| | | | |
|---|---|---|---|
| 4,036,825 A | 7/1977 | Fuchs et al. | |
| 4,066,638 A | 1/1978 | Fuchs et al. | |
| 4,585,460 A | 4/1986 | Schwander et al. | |
| 4,799,934 A * | 1/1989 | Lim et al. ........................ | 8/414 |
| 4,992,589 A | 2/1991 | Fuchs et al. | |
| 5,391,718 A | 2/1995 | Tzikas et al. | |
| 5,530,104 A | 6/1996 | Tzikas et al. | |
| 5,731,421 A | 3/1998 | Tzikas et al. | |
| 5,972,044 A * | 10/1999 | Braun et al. ..................... | 8/405 |

FOREIGN PATENT DOCUMENTS

| | | | |
|---|---|---|---|
| DE | 2 154 942 | | 5/1973 |
| DE | 34 41 273 | | 5/1986 |
| DE | 19813937 | * | 9/1999 |
| EP | 107 614 | | 5/1984 |
| EP | 171 611 | | 2/1986 |
| EP | 559 617 | | 2/1993 |
| EP | 688767 | * | 12/1995 |
| EP | 888768 A2 | * | 4/1998 |
| GB | 1 414 420 | | 11/1975 |

OTHER PUBLICATIONS

Matsui et al., "Synthesis and Reactivity of Primary Condensation Products of 1,3-difluoro-4,6-dinitrobenzene," Journal of the Chemical Society of Japan 68(3), 507-11, 1965.*
Nalwa, et al., Two-dimensional charge-transfer molecules for second order non-linear optics; synthesis, characterization, and second harmonic generation of N,N'-dialkyl-2,4-dinitro-1,5-diaminobenzene compounds, Journal of material science (1998) 3699-3710.*
Derwent Abstract of DE 19813937, Sep. 1999.*
JP 75 025 529—Abstract.

* cited by examiner

*Primary Examiner*—Margaret Einsmann
(74) *Attorney, Agent, or Firm*—Novak Druce DeLuca & Quigg

(57) ABSTRACT

The present invention relates to novel reactive dyes of formula I, (I), in which the variable independently denote X hydrogen, $NO_2$, or $NR^3R^4$, Y $NR^5R^6$, $OR^7$, $SR^8$, or $SO_2R^9$ or a group suitable as a leaving group under the conditions of nucleophilic, aromatic substitution, $R^1$ to $R^9$ independently hydrogen, $C_1$–$C_8$ alkyl, $C_2$–$C_8$ alkyl, in which non-adjacent $CH_2$ groups can be replaced by oxygen atoms, imino groups, or $C_1$–$C_4$ alkylimino groups, and/or $CH_2$ groups may be replaced by carbonyl groups, $C_2$–$C_8$ alkenyl, or a group containing an active site or the precursor of an active site, with the proviso that at least one group $R^1$ to $R^9$ is present which contains an active site or the precursor of an active site. The present invention also relates to the use of the reactivedyes of formula I for dyeing substrates containing nucleophilic groups, and to compositions containing at least one reactive dye of formula I.

8 Claims, No Drawings

REACTIVE DYES AND THE USE THEREOF FOR DYEING SUBSTRATES CONTAINING NUCLEOPHILIC GROUPS

DESCRIPTION

The present invention relates to novel reactive dyes of formula I

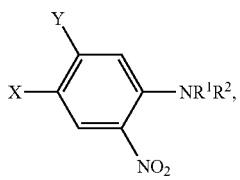

in which the variables independently denote

X hydrogen, $NO_2$, or $NR^3R^4$,

Y $NR^5R^6$, $OR^7$, $SR^8$, or $SO_2R^9$ or a group suitable as leaving group under the conditions of nucleophilic, aromatic substitution, $R^1$ to $R^9$ independently hydrogen, $C_1$–$C_8$ alkyl, $C_2$–$C_8$ alkyl, in which non-adjacent $CH_2$ groups can be replaced by oxygen atoms, imino groups or $C_1$–$C_4$ alkylimino groups, and/or $CH_2$ groups by carbonyl groups, $C_2$–$C_8$ alkenyl or a group containing an active site or the precursor of an active site, with the proviso that at least one of the radicals $R^1$ to $R^9$ is a group which contains an active site or the precursor of an active site.

The present invention also relates to the use of the reactive dyes of formula I for dyeing substrates containing nucleophilic groups.

The present invention also relates to compositions containing at least one reactive dye of formula I.

A large number of reactive dyes has been described for coloring a great variety of substrates. For example, the use of reactive dyes for dyeing nitrogen atom-containing fibers, such as wool, is disclosed in the specifications U.S. Pat. No. 4,066,638, EP 107,614, EP 559,617, DE 3,441,273, and DE 2,154,942.

U.S. Pat. No. 4,102,641 relates to the use of dyes containing a halogen triazine radical as fiber-reactive group for dyeing hair.

Furthermore, specification JP 75,025,529 A mentions dye formulations for dyeing hair. The reactive dyes used are based on p-sulfatoethylsulfonylaniline as diazo component and a fiber-reactive radical.

It is now the object of the present invention to provide further reactive dyes which show good interaction properties on the substrates to be dyed and can be applied under a variety of dyeing conditions.

Accordingly, we have found the above reactive dyes of the general formula I.

In instances where $R^1$ to $R^9$ correspond to radicals containing acidic hydrogen atoms, the reactive dyes of formula I are usually present in protonated form. Of course, the reactive dyes may also exist in the form of their, preferably physiologically acceptable, salts.

In the latter case, suitable cations are derived from, in particular, metal or ammonium ions. These primarily include lithium, sodium, or potassium ions or unsubstituted or substituted ammonium cations. Substituted ammonium cations are, for example, monoalkyl, dialkyl, trialkyl, tetraalkyl, or benzyltrialkylammonium cations or such cations as are derived from nitrogen-containing five-membered or six-membered saturated heterocyclic compounds, such as pyrrolidinium, piperidinium, morpholinium, piperazinium, or N-alkylpiperazinium cations or their N-monoalkyl or N,N-dialkyl-substituted products. By alkyl we generally mean linear or branched $C_1$–$C_{20}$ alkyl, which can be substituted by 1 or 2 hydroxyl groups and/or may be interspersed by from 1 to 4 oxygen atoms in ether-like fashion.

Examples of suitable $C_1$–$C_8$ alkyl represented by $R^1$ to $R^9$ are branched or unbranched alkyl chains, such as methyl, ethyl, n-propyl, isopropyl, n-butyl, sec-butyl, isobutyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, or 2-ethylhexyl.

As examples of suitable $C_2$–$C_8$ alkenyl represented by $R^1$ to $R^9$ there may be mentioned branched or unbranched alkenyl chains, such as vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl, or 2-octenyl.

Examples of suitable $C_2$–$C_8$ alkyl, in which non-adjacent $CH_2$ groups can be replaced by oxygen atoms, imino groups, or $C_1$–$C_4$ alkylimino groups, and/or $CH_2$ groups may be replaced by carbonyl groups, as represented by $R^1$ to $R^9$ are, eg, —$(CH_2$—$CH_2$—O—$)_p$H, —$(CH_2$—$CH_2$—O—$)_p$$CH_3$, —$(CH_2$—$CH(CH_3)$—O—$)_p$H, —$(CH_2$—$CH_2$—NR—$)_p$H, —$(CH_2$—$CH_2$—NR—$)_p$$CH_3$ or —$(CH_2$—CH($CH_3$)—NR—$)_p$H, where p denotes 1 or 2, or —$CH_2$—OC(O)—$[(CH_2)_R]$H, —$CH_2$—C(O)—O—$[(CH_2)_r]$H, —$CH_2$—NR—C(O)—$[(CH_2)_r]$H and —$CH_2$—C(O)—NR—$[(CH_2)_r]$H, where r denotes 0, 1, 2, 3, 4, or 5 and R independently denotes hydrogen, methyl, ethyl, n-propyl, isopropyl, n-butyl, sec-butyl, isobutyl, or tert-butyl.

The latter formulas cover, for example, the radicals —$CH_2$—O—C(O)—H and —$CH_2$—C—(O)—O—H (in each case r is 0), —$CH_2$—O—C(O)—$CH_3$ and —$CH_2$—C(O)—O—$CH_3$ (in each case r is 1), and —$CH_2$—O—C(O)—$C_2H_5$ and —$CH_2$—C(O)—O—$C_2H_5$ (in each case r is 2).

The following remarks apply to the meaning of radicals $R^1$ to $R^9$ when they denote a group containing an active site or the precursor of an active site. For the sake of simplicity, a group containing an active site or the precursor of an active site is referred to below a "reactive group".

If the reactive groups take part in an addition reaction with the relevant groups in the substrate, eg, with the amino or hydroxy groups of hair, this means, for example with reference to the vinyl sulfone site, that the amino or hydroxy groups in the hair are added to the reactive groups as follows:

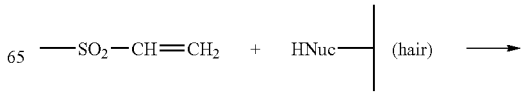

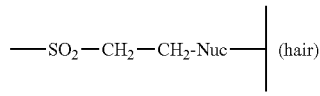 (hair)

When, on the other hand, the reactive groups take part in a substitution reaction with the relevant nucleophilic groups (HNuc-) in the substrate, eg, with the amino or hydroxy groups in hair, this means, for example with reference to the chlorotriazine site, that the leaving groups or atoms (eg, in this case chlorine) in the reactive groups are substituted by the amino groups in hair according to the following diagram:

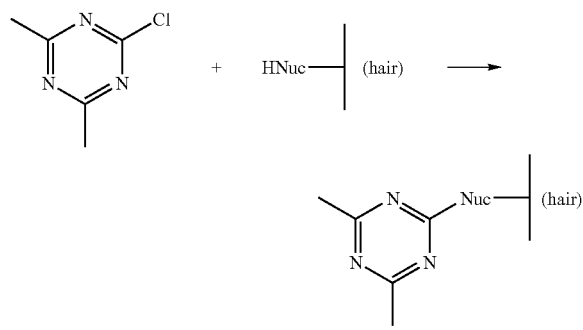

Additively reacting groups represented by $R^1$ to $R^9$ are, for example, acryloyl, monochloroacryloyl, dichloroacryloyl, or trichloroacryloyl, monobromoacryloyl, dibromoacryloyl, or tribromoacryloyl, CO—CCl=CH—COOH, —CO—CH=C—Cl—COOH, 2-chloropropionyl, 1,2-dichloropropionyl, 1,2-dibromopropionyl, 3-phenylsulfonylpropionyl, 3-methylsulfonylpropionyl, 2-sulfatoethylaminosulfonyl, 2-chloro-2,3,3-trifluorocyclobutylcarbonyl, 2,2,3,3-tetrafluorocyclobutylcarbonyl, 2,2,3,3-tetrafluorocyclobutylsulfonyl, 2-(2,2,3,3-tetrafluorocyclobutyl)acryloyl, 1- or 2-alkylsulfonylacryloyl or 1- or 2-arylsulfonylacryloyl, such as 1- or 2-methylsulfonylacryloyl.

Examples of suitable radicals $R^1$ to $R^9$, as (additively reacting) groups containing the precursor of an active site, are, in particular, $-M^1$-$SO_2$—$C_2H_4Q$, where $M^1$ stands for phenylene or linear or branched $C_1$–$C_8$ alkene in which non-adjacent $CH_2$ groups may be replaced by oxygen atoms, imino groups or $C_1$–$C_4$ alkylimino groups. For example, these are $CH_2$, $(CH_2)_2$, $(CH_2)_3$, $(CH_2)_4$, $CH(CH_3)CH_2$, $CH(CH_3)CH(CH_3)$, $(CH_2)_5$, $(CH_2)_6$, $(CH_2)_2O(CH_2)_2$, $(CH_2)_3$ $O(CH_2)$, $(CH_2)_2O(CH_2)_2O(CH_2)_2$, $(CH_2)_2NH$ $(CH_2)_2$, $(CH_2)_3NH(CH_2)_2$, $(CH_2)_2NH(CH_2)_2NH(CH_2)_2$,

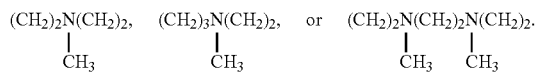

The radical Q stands for a group that is capable of being split off under alkaline reaction conditions, such as chlorine, bromine, $C_1$–$C_4$ alkylsulfonyl, phenylsulfonyl, $OSO_3H$, $SSO_3H$, $OP(O)(OH)_2$, $C_1$–$C_4$ alkylsulfonyloxy, phenylsulfonyloxy, $C_1$–$C_4$ alkanoyloxy, $C_1$–$C_4$ dialkylamino or a radical of the formula

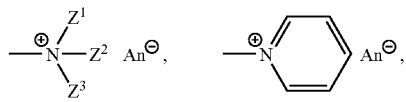

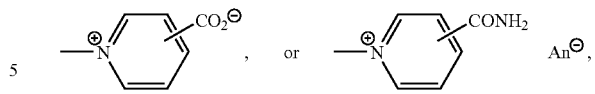

where $Z^1$, $Z^2$, and $Z^3$ are the same or different and independently denote $C_1$–$C_4$ alkyl or benzyl, and An⊖ denotes an equivalent of an anion. Suitable anions include, for example, fluoride, chloride, bromide, iodide, monochloro, dichloro, or trichloroacetate, methane sulfonate, benzene sulfonate or 2- or 4-methylbenzene sulfonate.

Preferred radicals Q are chlorine, acetate, and $SSO_3H$ and, more preferably, Q stands for $OSO_3H$.

An example of a suitable group containing an active site, as represented by $R^1$ to $R^9$, is, in particular, $-M^1$-$SO_2$—$CH=CH_2$, in which the variable $M^1$ has the meaning stated above.

Other (additively reacting) groups containing an active site or the precursor of an active site, are, for example, groups of formulas IIa to IIe, where U designates either —$C_2H_4Q$, as defined above, or a vinyl group.

(IIa)

(IIb)

(IIc)

(IId)

(IIe)

or (IIf)

Examples of substitutively reacting reactive groups represented by $R^1$ to $R^9$ are halogen-substituted radicals derived from 1,3,5-triazine, quinoxaline, phthalazine, pyrimidine, pyridazine, or 2-alkylsulfonylbenzthiazol as heterocyclic parent substances.

Particular mention may be made here of the following heterocyclic radicals which may additionally contain additively reacting substituents:

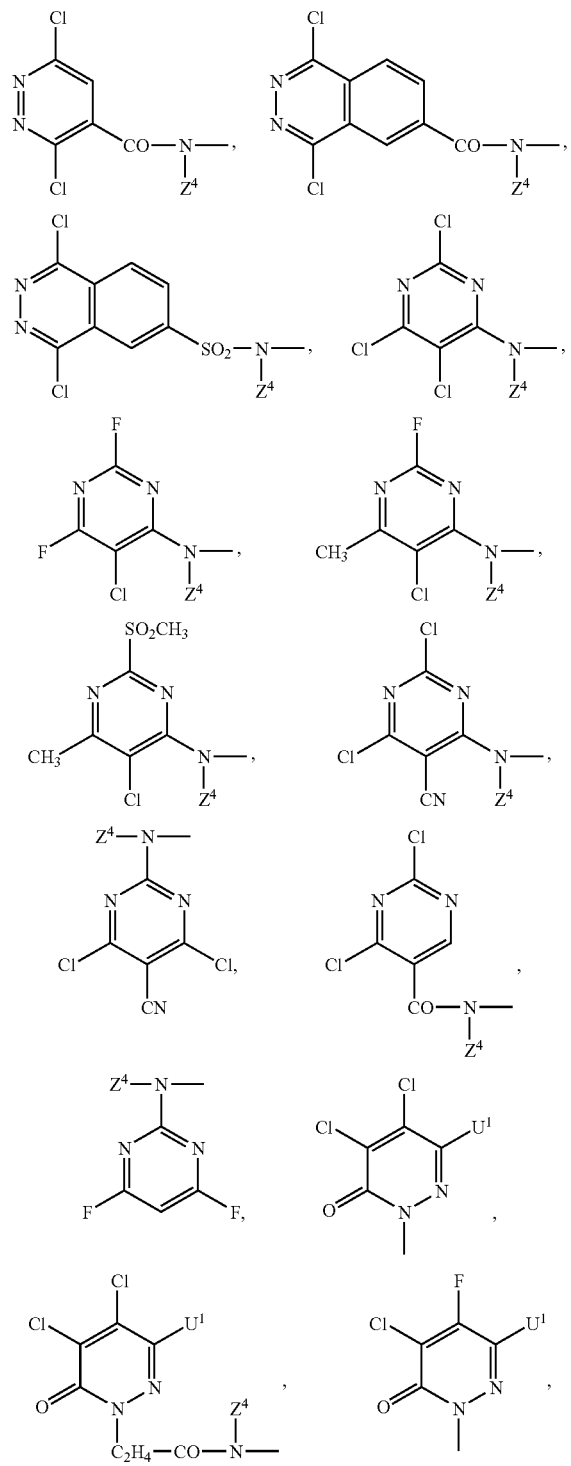

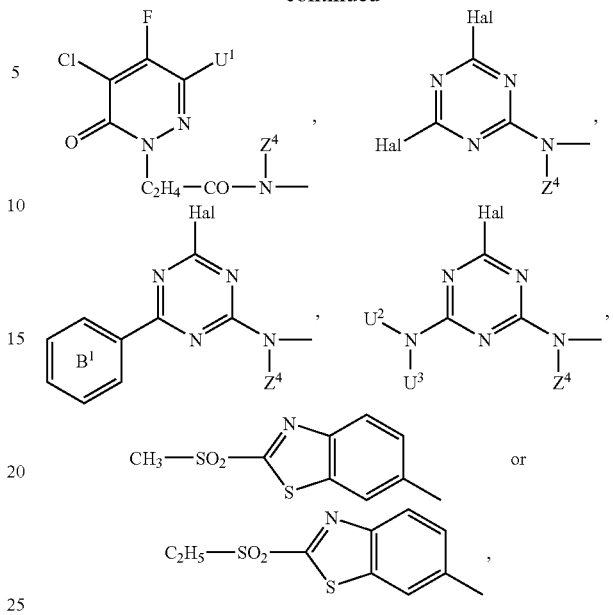

in which $Z^4$ independently stands for hydrogen, $C_1$–$C_6$ alkyl, or phenyl,

Hal denotes fluorine, chlorine, or bromine and $U^1$ denotes hydrogen or nitro, $U^2$ and $U^3$ independently denote hydrogen or $C_1$–$C_6$ alkyl, optionally substituted by hydroxy, halogen, cyano, hydroxysulfonyl or a radical of the formula —$SO_2$—U, where U has the meaning stated above, and optionally interspersed by 1 or 2 non-adjacent oxygen atoms, imino groups or $C_1$–$C_4$ alkylimino groups, or $U^2$ and $U^3$ form, together with the interconnecting nitrogen atom, a pyrrolidinyl, piperidinyl, morpholinyl, piperazinyl or N—($C_1$–$C_4$ alkyl)piperazinyl radical, or $U^2$ denotes a radical of the formula

in which the rings $B^1$ and $B^2$ may be monosubstituted or disubstituted by hydroxysulfonyl and/or benzoanellated, and ring $B^2$ may independently be monosubstituted or disubstituted by chlorine, nitro, $C_1$–$C_4$ alkyl, $C_1$–$C_4$ alkoxy, cyano, carboxyl, acetylamino, hydroxysulfonylmethyl or a radical of the formula $CH_2$—$SO_2$—U, $SO_2$—U, NH—CO—U, or $NU^2$—CO—$NU^2$-L-$SO_2$—U, in which U and $U^2$ have the aforementioned meanings and L stands for $C_2$–$C_6$ alkene, optionally substituted by hydroxy, chlorine, cyano, carboxyl, $C_1$–$C_4$ alkoxycarbonyl, $C_1$–$C_4$ alkanoyloxy or sulfato and optionally interspersed by 1 or 2 non-adjacent oxygen atoms, imino groups, or $C_1$–$C_4$ alkylimino groups.

Suitable radicals $U^2$ and $U^3$ include, for example, methyl, ethyl, propyl, isopropyl, butyl, isobutyl, sec-butyl, tert-butyl, pentyl, isopentyl, neopentyl, tert-pentyl, hexyl, or 2-methylpentyl.

Examples of other radicals $U^2$ and $U^3$ are hydroxy($C_1$–$C_4$ alkyl), such as hydroxymethyl, 1-hydroxyethyl-1, 2-hydroxyethyl-1, 1-hydroxypropyl-1, 2-hydroxypropyl-1, 3-hydroxypropyl-1, 1-hydroxypropyl-2, 2-hydroxypropyl-2, 1-hydroxybutyl-1, 2-hydroxybutyl-1, 3-hydroxybutyl-1, 4-hydroxybutyl-1, 1-hydroxybutyl-2, 2-hydroxybutyl-2, 1-hydroxybutyl-3, 2-hydroxybutyl-3, 1-hydroxy-2-methylpropyl-3, 2-hydroxy-2-methylpropyl-3, 3-hydroxy-2-methylpropyl-3, or 2-hydroxymethylpropyl-2.

Examples of other radicals $U^2$ and $U^3$ are cyanomethyl, cyanoethyl, cyanopropyl, or cyanobutyl and also hydroxysulfonylmethyl, 2-hydroxysulfonylethyl, 2- or 3-hydroxysulfonylpropyl, or 2- or 4-hydroxysulfonylbutyl.

The radical L is, eg, $(CH_2)_2$, $(CH_2)_3$, $(CH_2)_4$, $CH(CH_3)CH_2$, $CH(CH_3)CH(CH_3)$, $(CH_2)_5$, or $(CH_2)_6$.

The radical L may also be, for example, $(CH_2)_2O(CH_2)_2$, $(CH_2)_3O(CH_2)_2$, $(CH_2)_2O(CH_2)_2O(CH_2)_2$, $(CH_2)_2S(CH_2)_2$, $(CH_2)_3S(CH_2)_2$, $(CH_2)_2S(CH_2)_2S(CH_2)_2$, $(CH_2)_2NH(CH_2)_2$, $(CH_2)_3NH(CH_2)_2$, $(CH_2)_2NH(CH_2)_2(CH_2)_2$,

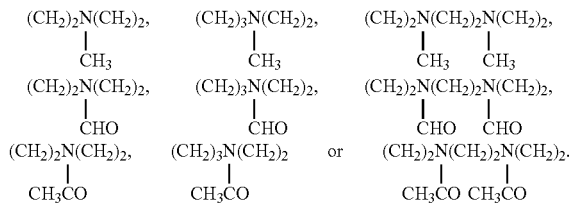

Y in formula I corresponds to the radicals $NR^5R^6$, $OR^7$, $SR^8$, or $SO_2R^9$ or a group that is suitable as a leaving group under the conditions of nucleophilic, aromatic substitution, the definitions of $R^5$ to $R^9$ being the same as those stated above. In the case of the radical $NR^5R^6$, $R^5$ and $R^6$ can be the same or different.

Any of the groups that are known to the person skilled in the art as being suitable therefore, may function as leaving groups. Thus, for example, aliphatic or aromatic sulfonic acid derivatives, and also the aliphatic sulfonic acid derivatives partially or completely substituted by fluorine are suitable for this purpose.

Examples of Y as a suitable group to function as a leaving group under the conditions of nucleophilic, aromatic substitution, are

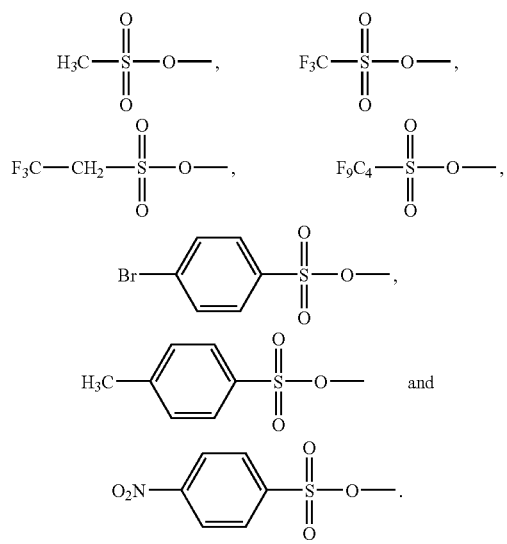

Mention may also be made here of fluorine, chlorine, bromine, or the group

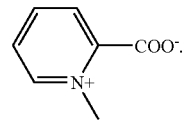

When Y is equivalent to the substituents $SO_2$—$CH$=$CH_2$ or $SO_2$—$C_2H_4Q$ (Y corresponds in such cases to $SO_2R^9$ where $R^9$ is a vinyl group and the group —$C_2H_4Q$ respectively), this should be regarded, for the purposes of the invention, as a group containing an active site or the precursor of an active site. The remaining radicals $R^1$ to $R^8$ can, but need not, be further groups containing an active site or the precursor of an active site.

Preferred reactive dyes of the invention are those in which X denotes $NO_2$.

Further preferred reactive dyes, also in respect of the aforementioned preferred embodiment, are those in which Y denotes $SR^8$, $SO_2R^9$, or a group that is suitable for use as a leaving group under the conditions of nucleophilic, aromatic substitution.

We particularly claim reactive dyes of formula I and aforementioned preferred embodiment relating to when X denotes $NO_2$, in which Y corresponds to $SR^8$, $SO_2R^9$, fluorine, chlorine, bromine or a group

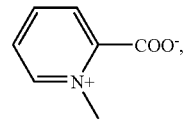

fluorine being particularly preferred.

The present invention also relates to the use of the reactive dyes of the invention and to their preferred embodiments for dyeing substrates containing nucleophilic groups.

Such substrates comprise, for example, a great variety of grades of cellulose products, such as textiles based on cotton, paper for the production of newspapers and magazines, cellulosic material for, say, sanitary purposes, and wooden products, for example for the production of furniture, hides, such as leather, and animal skins, also human skin, for example when applying temporary tattoos, and human hair.

The reactive dyes of the invention and their preferred embodiments are preferably used for dyeing substrates containing hydroxy, mercapto, amino, and/or imino groups.

In particular, the reactive dyes of the invention and their preferred embodiments are used for dyeing keratinic fibers, of which animal or human hair is particularly significant.

The present invention also relates to compositions containing at least one reactive dye of the invention.

The reactive dyes of the invention are usually employed in dissolved form. For preferred cosmetic applications the reactive dyes are dissolved in an aqueous, cosmetically acceptable medium.

In this aqueous cosmetically acceptable vehicle the pH varies between pH 3 to pH 11, more preferably pH 6 to pH 11. It is set to the desired value by means of inorganic or organic bases, salts of weak acids, or buffers. By way of example there can be mentioned ammonia, ammonium, potassium, or sodium carbonate, sodium hydroxide, mono-, di- or tri-ethanolamine, disodium hydrogenphosphate, sodium citrate, or sodium borate.

The reactive dyes are present in said compositions in concentrations of from 0.01 to 10 wt %, based on the total weight of the composition.

Common auxiliaries in compositions for hair coloration are anionic, cationic, non-ionic, or amphoteric surface-active compounds or mixtures thereof. Examples of surface-active compound are soaps, alkylbenzene sulfonates, alkyl naphthalenesulfonates, sulfates, fatty alcohol polyglycol sulfates, and sulfonates of fatty alcohols, quarternary ammonium salts, such as trimethylcetylammonium bromide, cetylpyridinium bromide, quaternium 1 to X (INCI), cocoyltrimethylammonium methylsulfate (INCI), hydroxyethyl cetyldimomium phosphates (INCI), cetyltrimethylammonium chloride, optionally oxyethylenized fatty acid ethanolamides, polyoxyethylenized acids, alcohols, and amines, polyglycerolized alcohols, polyoxyethylenized or polyglycerolized alkyl phenols, and also polyoxyethylenized alkyl sulfates. The surface-active compounds are present in the compositions of the invention in a concentration of from 0.5 to 40 wt %, based on the total weight the preparation.

Other conventional auxiliaries are organic solvents acting as solubilizing agents, eg, $C_1$–$C_4$ alcohol such as ethanol and isopropanol, glycols, glycol ethers, such as ethylene glycol, propylene glycol, 2-methoxyethanol, 2-ethoxyethanol, or 2-butoxyethanol, and also glycerol. These solvents are usually present in a concentration of 0–40 wt %, based on the total weight of the composition.

In order to simplify handling of the compositions of the invention, thickeners are usually added as auxiliaries. Common thickeners are cellulose derivatives, such as methyl, hydroxymethyl, hydroxyethyl, hydroxypropyl, or carboxymethyl cellulose, sodium alginate, gum arabic, gum xanthan, gum traganth, acrylic acid polymers, polyvinylpyrrolidone, poly(vinyl acetate-co-crotonic acid)s, poly(vinyl acetate-co-vinyl pyrrolidone)s, poly(butylvinyl ether-co-maleic anhydride)s, or poly(methylvinyl ether-co-maleic anhydride)s. Inorganic thickener, such as bentonite, are also suitable. These thickeners are usually employed in a concentration of up to 5 wt %, based on the total weight of the composition.

Hair-care compositions which are to be used in the form of gels also contain gel-forming substances, such as carbomers (INCI). To acquire certain care-promoting properties, the compositions may additionally contain cationic polymers and silicone compounds. Suitable cationic polymers are, for example, polyquaternium 1 to x (INCI), copolymers of vinyl pyrrolidone/vinyl imidazolium salts (Luviquat® FC, Luviquat® HM;, sold by BASF Aktiengesellschaft, Ludwigshafen), copolymers of vinyl pyrrolidone/dimethylaminoethyl methacrylate, quaternized with diethyl sulfate (Luviquat PQ 11); cationic cellulose derivatives (polyquaternium 4 and 10), acrylamide copolymers (polyquaternium 7) and cationic guar gum derivatives, eg, guar hydroxypropyltriminium chloride (INCI). Suitable silicone compounds are, for example, alkyl polysiloxanes, polyaryl siloxanes, polyarylalkyl siloxanes, polyether siloxanes, or silicone resins.

Further conventional auxiliaries are mild antioxidants that do not react with the dyes, penetrating agents, sequestering agents, buffers, perfume oils, light-stabilizing agents (UV-A and UV-B filters), preservatives, shampoos, and active substances such as (d(+)-pantothenyl alcohol, bisabolol and vitamins, eg, vitamins A, C, and E.

The compositions of the invention can be used in liquid form, usually thickened, as a cream, paste, gel, or any other suitable form.

The hair colouring compositions of the present invention may, in addition to the dyes discussed herein above include other nonoxidative, oxidative and other dye materials. Optional nonoxidative and other dyes suitable for use in the hair colouring compositions and processes according to the present invention include demi-permanent, semi-permanent, temporary and other dyes. Non-oxidative dyes as defined herein include the so-called "direct action dyes", metallic dyes, metal chelate dyes, fibre reactive dyes, acid dyes, basic dyes, non-ionic dyes, anionic dyes, cationic dyes, HC dyes and other synthetic and natural dyes.

Oxidative hair colouring agents to be used in the compositions herein are typically, but without intending to be limited thereby, oxidative hair colouring agents, consisting essentially of at least two components, which are collectively referred to as dye forming intermediates (or precursors). Dye forming intermediates can react in the presence of a suitable oxidant to form a coloured molecule. The dye forming intermediates used in oxidative hair colorants include: aromatic diamines, aminophenols, various heterocycles, phenols, naphthols and their various diaminobenzene or its derivatives.

The hair colouring compositions may also comprise at least one oxidising agent, which may be an inorganic or organic oxidising agent.

The oxidising agent is preferably present in the colouring composition at a level of from about 0.01% to about 20%, more preferably from about 0.01% to about 10%, more preferably from about 1% to about 6% by weight of the composition. A preferred oxidising agent for use herein is an inorganic peroxygen oxidising agent.

In the preferred application, a hair-care composition is applied to the hair and allowed to act thereon over a period of from 5 to 50 minutes and preferably from 10 to 30 minutes, after which the hair is rinsed and optionally washed with a conventional shampoo.

Dyeing can be accelerated by using the composition in a warm state or by applying heat externally, or intensified if the period of action is not shortened. Preferably, temperatures ranging from 20° to 40° C. are used.

The reactive dyes of the invention yield level dyeings and cover even white hair well. The dyeings show good fastness to light, washing, weathering, and abrasion, as external influences.

Generally reactive dyes, by reason of their different dyeing mode, make it possible to do without $H_2O_2$ as oxidizing agent in the dyeing process. Particularly advantageous is the fact that the shade is determined by the dye and is not developed in the hair, which simplifies the preparation of dyestuff blends and the production of various shades.

EXAMPLE 1a

Production of 2-hydroxyethyl-2'-aminoethylsulfone 245 g (2.4 mol) of 96% strength sulfuric acid were added to 400 g of ice. 484 g (4 mol) of 2-aminoethyl-2'-hydroxyethylsulfide (produced as described in J. R. Lotz, B. P. Block, W. C. Fernelius, J. Phys. Chem., 63 (1959), pp 541) were then added dropwise within a period of 30 minutes, during which process the temperature rose to 45° C. 1 g (0.004 mol) of sodium tungstate (sold by Merck KGaA, Darmstadt) and 10 g of citric acid (sold by Merck KGaA, Darmstadt) were then added, and the mixture was adjusted to pH 4.5 with 20% strength sodium hydroxide solution and heated to 80° C. 953 g (8.4 mol) of a 30% strength hydrogen peroxide solution were added dropwise within a period of 3 hours while the pH was kept between 4.5 and 5 with 20% strength sodium hydroxide solution.

The peroxide excess was destroyed with sodium sulfite, the solution concentrated in a rotary film evaporator, and there were added, portionwise, a total of 1500 mL of ethanol. After each shot of ethanol, the mixture was concentrated, and finally the remaining oil was caused to crystallize by the addition of 200 mL of methanol. There were obtained 775 g (3.85 mol) of 2-hydroxyethyl-2'-aminoethylsulfone.

EXAMPLE 1b

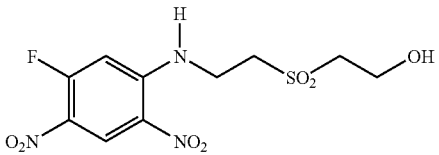

21 g (0.1 mol) of 1,5-difluoro-2,4-dinitrobenzene (sold by Clariant(Deutschland) GmbH, Frankfurt) and 0.5 g of Emulan® EL (sold by BASF Aktiengesellschaft, Ludwigshafen) were stirred in 30 mL of water and 70 mL of acetone. To this mixture there were added dropwise, at room temperature, 33.1 g (0.1 mol) of 2-hydroxyethyl-2'-aminoethylsulfone (produced as described in Example 1a) in the form of the sulfate. During this operation, the pH was kept between 6 and 7 by simultaneous addition of sodium hydrogencarbonate. Stirring was continued over a period of 2 hours, and the resulting precipitate was then filtered off. Following drying, there were obtained 112 g of the stated compound. The structure was determined by NMRspectroscopy.

EXAMPLE 1c

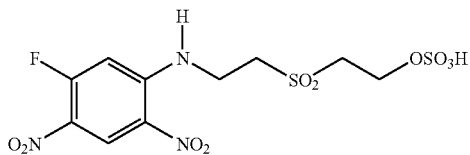

27 g (0.08 mol) of the hydroxy compound of Example 1b were added to 80 mL of 96% strength sulfuric acid at from 0° to 5° C. Stirring was continued over a period of two hours at from 0° to 5° C. and then for a further 15 hours at room temperature. The reaction mixture was added to 100 mL of ice water such that the temperature did not exceed 5° C. The mixture was heated to room temperature and the product salted out with 60 g of potassium chloride. The product of the above formula was filtered off in vacuo and dried in vacuo at 25° C. There were obtained 39.8 g of the product having a purity of 98.4% (HPLC % by area).

EXAMPLE 1d

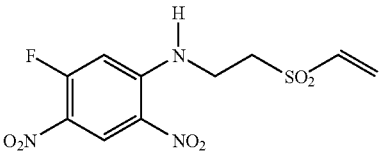

20 g (0.04 mol) of the sulfuric acid half-ester of Example 1° C. were added to 200 mL of water. The pH was adjusted to from 8.5 to 9, and kept at said value, with solid soda. The batch was then stirred for 2 h at 35° C. and for a further 15 h at room temperature. The batch was then set to pH 7 with 20% strength hydrochloric acid and the precipitated product filtered off. Following vacuum drying at 25° C., there were obtained 22.8 g of a product of the above formula. The purity was 95.4% (HPLC % by area).

EXAMPLE 2a

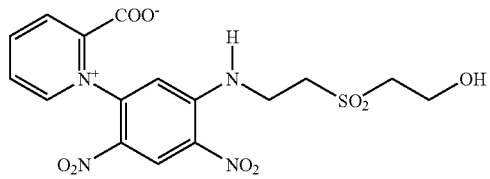

41 g (0.1 mol) of the ca 73% strength fluorine compound of Example 1b were added to 250 mL of water to which 0.1 g of Emulan® EL had been added. There were then added 14.8 g (0.12 mol) of nicotinic acid (sold by Fluka Chemie AG, Buchs, Switzerland) and the mixture was adjusted to pH 6 to 7 with sodium hydrogencarbonate. The mixture was heated to 60° C. over a period of 9 hours, the pH then raised to 7.5, and stirring was continued for a further 8 hours. The precipitated product of the above formula was filtered off and dried in vacuo at 35° C. The yield was 36.3 g.

EXAMPLE 2b

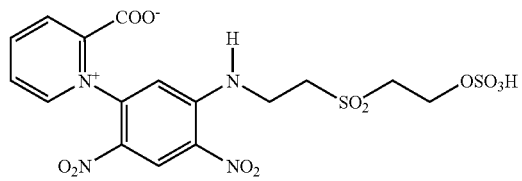

15 g (0.05 mol) of the hydroxy compound of Example 2a were added to 100 mL of 96% strength sulfuric acid at from 0° to 5° C. within a period of 30 minutes. Stirring was continued over a period of two hours at from 0° to 5° C. and then for a further 15 hours at room temperature. The reaction mixture was added to 110 mL of ice water such that the temperature did not exceed 5° C. The product of the above formula was filtered off in vacuo and dried in vacuo at 25° C. There were obtained 16.8 g of the product having a purity of 100% (HPLC % by area).

EXAMPLE 3

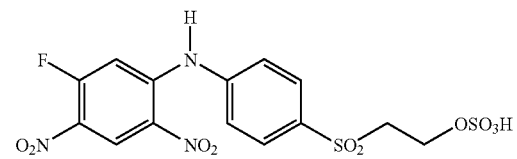

29.2 g (0.1 mol) of p-aminobenzenesulfatoethyl sulfonate (sold by Sajjan, Mumbai, India) were dissolved in 250 mL of water, the pH being adjusted to 4 with 10% strength sodium hydroxide solution. There were introduced 0.5 g of Emulan® EL followed by 21 g (0.1 mol) of 1,5-difluoro-2,4-dinitrobenzene. The pH was set to from 6 to 7, and kept at that value, with sodium hydrogencarbonate. Stirring was carried out for 5 hours at 30° C. The precipitated product of the above formula was filtered off and dried in vacuo at 35° C. The yield was 31.0 g.

EXAMPLE 4a

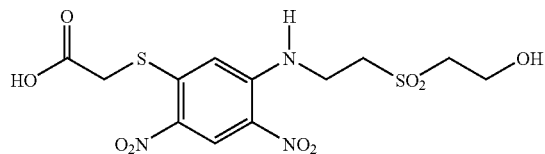

37 g (0.1 mol) of the fluorine compound of Example 1b were added to 250 mL of water and 0.2 g of Emulan® EL were added. 11 g (0.12 mol) of thioglycollic acid (sold by Merck KGaA, Darmstadt) were then added and the mixture was set to a pH of 6.5 with sodium hydrogencarbonate. The batch was heated to 40° C. and stirring was continued at this temperature over a period of 6 hours. Following cooling, the precipitated product was filtered off and dried in vacuo at 35° C. The yield was 33.9 g.

EXAMPLE 4b

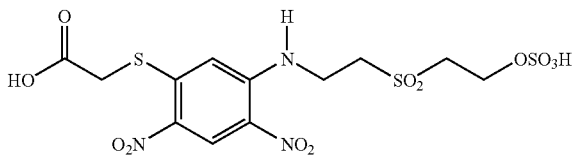

15.0 g of the hydroxy compound of Example 4a were added to 100 mL of 96% strength sulfuric acid at from 0° to 5° C. and stirred at this temperature over a period of two hours. During the following 17 hour stirring period, the temperature rose to from 20° to 25° C. The reaction mixture was added to 1000 mL of ice water and filtered. The filtrate was salted out with 15 g of potassium chloride, and the product was filtered off and dried in vacuo at 35° C. The yield was 14.4 g of the compound of the formula shown above.

EXAMPLE 5a

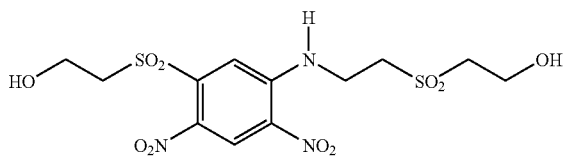

41.0 g (0.1 mol) of the compound of Example 1b were added to 250 mL of water and, following the addition of 0.1 g of Emulan® EL, suspended. 9.4 g (0.12 mol) of mercaptoethanol (sold by Merck KGaA, Darmstadt) were then added and the pH was set to from 5.5 to 6 with sodium hydrogencarbonate. Stirring was carried out for 5 hours at 35° C., the mixture then cooled to room temperature, and the resulting thioether was filtered off. The moist intermediate product (96 g) was stirred in 500 mL of water, and 0.3 g of sodium tungstate (sold by Merck KGaA, Darmstadt) were added, and the mixture was heated to 80° C. 63 g of 30% strength hydrogen peroxide solution were added dropwise at this temperature within a period of 3 hours. On cooling to room temperature, the sulfone was salted out with sodium chloride, filtered off, and dried.

There were obtained 42.3 g of the compound of the formula shown above (HPLC: 96.7% by area).

EXAMPLE 5b

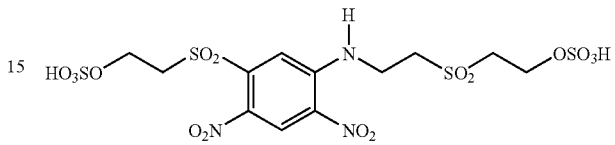

10.0 g of the hydroxy compound of Example 5a were added to 100 mL of 96% strength sulfuric acid at from 0° to 5° C. within a period of 45 min and stirred at this temperature over a period of two hours. During the following 17 hour stirring period, the temperature rose to from 200 to 25° C. The reaction mixture was slowly added to 1000 mL of ice water such that the temperature did not exceed 5° C.

The pH was set to 5 by the addition of calcium carbonate at from 5° to 10° C. The precipitated calcium sulfate was filtered off, and the filtrate set to pH 4.5 with acetic acid and concentrated to dryness at 30° C. in the vacuum of a rotary film evaporator. Further drying was carried out at room temperature in a vacuum drying cabinet. The yield of the product of the formula shown above was 20.3 g (HPLC 93.4% by area).

COLORATION EXAMPLE 1.25 g of the reactive dye of Example 1° C. were dissolved in 25 mL of water and the pH was adjusted to 7 with sodium hydrogenphosphate. A bleached skein of human hair (2 g) was immersed in the solution heated to 36° C. and the solution allowed to act at this temperature over a period of 20 minutes. The hair was then rinsed with water and dried in air. The hair was dyed an intense yellow. Under the same conditions, intense yellow hair colorations were likewise obtained using the reactive dyes of the invention described in Examples 1d, 2b, 3, 4b, and 5b.

FORMULATION EXAMPLES

A) Hair-coloring Cream

Phase I:

| | |
|---|---|
| 1.5 g | ceteareth-6 (and) stearyl alcohol (INCI) |
| 1.5 g | ceteareth-25 |
| 6.0 g | cetearyl octanoate |
| 3.0 g | cetearyl alcohol |

Phase II:

| | |
|---|---|
| 2 g | reactive dye of formula 1° C. |
| 2 g | propylene glycol |
| 84 g | dest. water |
| q.s. | citric acid/triethanolamine for adjustment to pH 7 |
| q.s. | preserving agent |

Phase III:

| | |
|---|---|
| q.s. | perfume oil |

The ingredients were dissolved at 60° C., and phase I was added to phase II. After cooling to 30° C., phase III was added.

A bleached skein of human hair (2 g) was treated with 0.5 g of the dyeing creme, which was allowed to act for 20 min. A water-rinse followed. There was obtained a hair coloration as described in the coloration example.

B) Hair-coloring Lotion

| | |
|---|---|
| 5 g | reactive dye of formula 1c |
| 1.2 g | Natrosol ® 250 HR (sold by Aqualon/Hercules Inc. Wilmington, Delaware, US-A), (hydroxyethylcellulose (INCI)) |
| 1 g | propylene glycol |
| ad 100 g | dest. water |
| q.s. | preserving agent |

A bleached skein of human hair (2 g) was treated with 0.5 g of the dyeing lotion, which was allowed to act for 20 min. A water-rinse followed. There was obtained a hair coloration as described in the coloration example.

C) Hair-coloring Mousse

| | |
|---|---|
| 2 g | reactive dye of formula 1c |
| 3 g | Luviskol ® VA 64 (sold by BASF Aktiengesellschaft, Ludwigshafen), (PVP/VA copolymer (INCI)) |
| 0.45 g | ceteareth-25 (INCI) |
| 0.10 g | dimethicone (INCI) |
| 10 g | propane/butane |
| ad 100 g | dest. water |
| q.s. | preserving agent |

A bleached skein of human hair (2 g) was treated with 0.5 g of the hair-coloring mousse, which was allowed to act for 15 min, followed by a water rinse. In addition to the attainment of intense dyeing, the hair is very easy to comb and has a well-groomed appearance. There was obtained a hair coloration as described in the coloration example.

D) Hair-coloring Shampoo

| | |
|---|---|
| 5 g | reactive dye of formula 1c |
| 40 g | sodium laurylethersulfate (INCI) (Texapol ® N 28;, sold by Henkel KGaA, Dusseldorf) |
| 10 g | Tego ® Retain L 7 (sold by Goldschmidt AG Degussa AG, Dusseldorf) (cocamidopropyl betaine (INCI)) |
| 2 g | Gluatin WQ (wheat germ protein) |
| ad 100 g | dest. water |
| q.s. | preserving agent |
| q.s. | common salt as thickener |

The use of a hair-coloring shampoo makes it possible to clean and dye the hair in one. A bleached skein of human hair (2 g) was treated with 0.5 g of the hair-coloring shampoo and after 1 min rinsed until no more foaming occurred. There was obtained a hair coloration as described in the coloration example.

E) Coloring Paste

| | |
|---|---|
| 2 g | reactive dye of formula 1c |
| 7 g | titanium(IV) oxide |
| 15 g | Aerosil ® (sold by Degussa AG, Dusseldorf) |
| 10 g | Lutrol ® F 127 (polyethylene glycol, sold by BASF Aktiengesellschaft, Ludwigshafen) |
| ad 100 g | dest. water |
| q.s. | preserving agent |

A bleached skein of human hair (2 g) was treated with 0.5 g of the hair-coloring paste, which was allowed to act for 15 min, followed by a water rinse. There was obtained a hair coloration as described in the coloration example.

F) Hair-coloring Shampoo

| | |
|---|---|
| 10 g | reactive dye of formula 1c |
| 2.20 g | gum xanthan (Keltrol ® T;, sold by Kelco Biopolymers, San Diego, California, US-A) |
| 20.0 g | sodium laurylethersulfate |
| 2.50 g | olein diethanolamide |
| 0.10 g | Trilon ® B (sold by BASF Aktiengesellschaft, Ludwigshafen) |
| ad 100 g | dest. water |
| q.s. | preserving agent |

25 g of the coloring paste were mixed with 25 mL of dest. water, and a bleached skein of human hair (2 g) was treated with this coloring shampoo, which was allowed to act for 20 min. A water-rinse followed. There was obtained a hair coloration as described in the coloration example.

G) Oxidative Hair Colouring Formulation

I. Dye Cream Emulsion

Weight % in Use

| | |
|---|---|
| q.s. | water |
| 24.75 | emulsion base |
| 4.0 | reactive dye of formula 3 |
| 4.125 | 30% aqueous ammonium hydroxide |

II. Emulsion Base

Weight % in Use

| | |
|---|---|
| q.s. | water |
| 1.5 | ceteareth 25 |
| 2.25 | cetyl alcohol |
| 2.25 | stearyl alcohol |
| 0.06 | sodium benzoate |
| 0.07 | phenoxyethanol |
| 0.08 | benzyl alcohol |
| 0.02 | tetrasodium EDTA |
| 2.0 | silicone (DC Q2-8220 from Dow Corning) |

III. Hydrogen Peroxide Emulsion Base

Weight % in Use

| | |
|---|---|
| q.s. | water |
| 4.2 | ceteareth 25 |
| 6.25 | cetyl alcohol |
| 6.25 | stearyl alcohol |

IV. Hydrogen Peroxide Cream
Weight % in Use

| | |
|---|---|
| 36 | hydrogenperoxide emulsion base |
| 17.7 | 35% hydrogen peroxide |
| q.s. | water |

The dye emulsion base is prepared by a one pot process as follows:
1. Add water to vessel. Heat to above the melt temperature of the fatty alcohols with agitation.
2. Add fatty alcohols and any ethoxylated fatty alcohols, e.g. ceteareth-25, cetyl, stearyl and steareth-2, and allow to melt. Increase agitation.
3. Continue mixing with shear.
4. Begin cooling with shear adding preservatives at appropriate temperature.
5. During cooling add silicone with mixing until homogeneous.
6. Cool to room temperature.

The hydrogen peroxide cream is also prepared similarly using a one pot process.

All 3 components are thoroughly mixed before application to hair for a 30 minute period, followed by a rinsing with water and dried. A hair colouration as described in the hair colouration example was obtained.

The invention claimed is:

1. A reactive dye of formula I

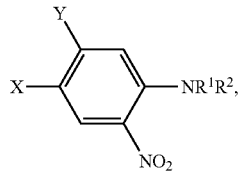
(I)

in which the variables independently denote
X NO$_2$,
Y NR$^5$R$^6$, OR$^7$, SR$^8$, SO$_2$R$^9$, or

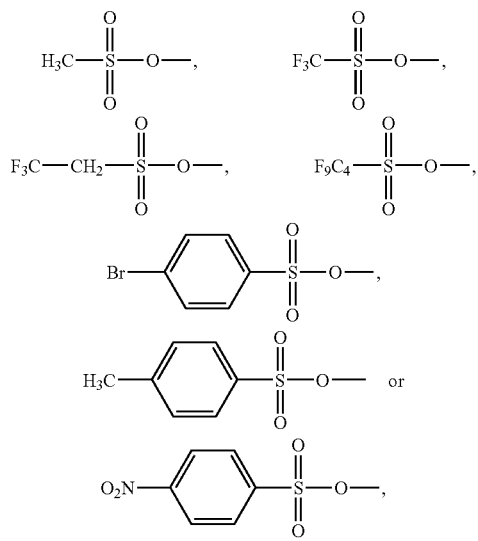

or fluorine, chlorine, bromine, or a group

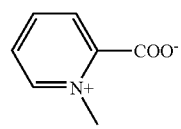

R$^1$, R$^2$ and R$^5$ to R$^9$ independently denote hydrogen, C$_1$–C$_8$ alkyl, C$_2$–C$_8$ alkyl, in which non-adjacent CH$_2$ groups can be replaced by oxygen atoms, imino groups, or C$_1$–C$_4$ alkylimino groups, and/or CH$_2$ groups may be replaced by carbonyl groups, or C$_2$–C$_8$ alkenyl, or an additively reacting group selected from the group consisting of acryloyl, monochloroacryloyl, dichloroacryloyl, trichloroacryloyl, monobromoacryloyl, dibromoacryloyl, tribromoacryloyl, —CO—CCl═CH—COOH, —CO—CH═CCl—COOH, 2-chloropropionyl, 1,2-dichloropropionyl, 1,2-dibromopropionyl, 3-phenylsulfonylpropionyl, 3-methylsulfonylpropionyl, 2-sulfatoethylaminosulfonyl, 2-chloro-2,3,3-trifluorocyclobutylcarbonyl, 2,2,3,3-tetrafluorocyclobutylcarbonyl, 2,2,3,3-tetrafluorocyclobutylsulfonyl, 2-(2,2,3,3-tetrafluorocyclobutyl)acryloyl, 1-alkylsulfonylacryloyl, 2-alkylsulfonylacryloyl, 1-arylsulfonylacryloyl, 2-arylsulfonylacryloyl, —(CH$_2$)$_2$—SO$_2$(CH$_2$)$_2$—OH, —(CH$_2$)$_2$—SO$_2$(CH$_2$)$_2$—OSO$_3$H, —(CH$_2$)$_2$—SO$_2$—CH═CH$_2$ and p-phenylsulfatoethyl-sulfonate, and wherein at least one of the radicals R$^1$, R$^2$ and R$^5$ to R$^9$ is a group containing an additively reacting group selected from the group consisting of acryloyl, monochloroacryloyl, dichloroacryloyl, trichloroacryloyl, monobromoacryloyl, dibromoacryloyl, tribromoacryloyl, —CO—CCl═CH—COOH, —CO—CH═CCl—COOH, 2-chloropropionyl, 1,2-dichloropropionyl, 1,2-dibromopropionyl, 3-phenylsulfonylpropionyl, 3-methylsulfonylpropionyl, 2-sulfatoethylaminosulfonyl, 2-chloro-2,3,3-trifluorocyclobutylcarbonyl, 2,2,3,3-tetrafluorocyclobutylcarbonyl, 2,2,3,3-tetrafluorocyclobutylsulfonyl, 2-(2,2,3,3-tetrafluorocyclobutyl)acryloyl, 1-alkylsulfonylacryloyl, 2-alkylsulfonylacryloyl, 1-arylsulfonylacryloyl, 2-arylsulfonylacryloyl, —(CH$_2$)$_2$—SO$_2$(CH$_2$)$_2$—OH, —(CH$_2$)$_2$—SO$_2$(CH$_2$)$_2$—OSO$_3$H, —(CH$_2$)$_2$—SO$_2$—CH═CH$_2$ and p-phenylsulfatoethyl-sulfonate.

2. A reactive dye as defined in claim 1, in which Y denotes SR$^8$, SO$_2$R$^9$, fluorine, chlorine, bromine or a group

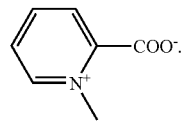

3. A reactive dye as defined in claim 1, in which Y denotes fluorine.

4. A method of dyeing a substrate containing nucleophilic groups, which comprises treating the substrate with an effective amount of the reactive dye defined in claim 1.

5. The method of claim 4, wherein the substrate contains hydroxy, mercapto, amino, and/or imino groups.

6. A method of dyeing keratinic fibers, which comprises treating the fibers with an effective amount of the reactive dye defined in claim 1.

7. The method of claim 6, wherein the fibers are animal or human hair.

8. A composition whenever containing at least one reactive dye as defined in claim 1.

* * * * *